United States Patent [19]

Fujiwara et al.

[11] Patent Number: 4,579,940
[45] Date of Patent: Apr. 1, 1986

[54] 14-DE(HYDROXYMETHYL)-MYCAMINOSYLTYLONOLIDE DERIVATIVES

[75] Inventors: Tatsuro Fujiwara; Hideyuki Watanabe; Takao Hirano, all of Shizuoka, Japan

[73] Assignee: Toyo Jozo Kabushiki Kaisha, Shizuoka, Japan

[21] Appl. No.: 676,858

[22] Filed: Nov. 30, 1984

[30] Foreign Application Priority Data

Nov. 30, 1983 [JP] Japan .................. 58-224487
Nov. 30, 1983 [JP] Japan .................. 58-224488
Dec. 1, 1983 [JP] Japan .................. 58-228256

[51] Int. Cl.$^4$ ............................ C07H 17/08
[52] U.S. Cl. ............................ 536/7.1
[58] Field of Search .................. 536/7.1, 7.2, 7.4; 424/180

[56] References Cited

U.S. PATENT DOCUMENTS 4,463,171 7/1984 Umezawa et al. ............ 536/7.1
4,490,524 12/1984 Fujiwara et al. ............ 536/7.1

FOREIGN PATENT DOCUMENTS 3301959 5/1982 Fed. Rep. of Germany .
3302690 5/1982 Fed. Rep. of Germany .
57005000 6/1980 Japan .
2081711 6/1981 United Kingdom .

OTHER PUBLICATIONS

Migrdichian *Organic Synthesis* pp. 332, 311 and 257, 1957.
Morrison et al. *Organic Chemistry* 3rd ed. p. 631, 1973.
"Synthesis of 4′-Deoxymycaminosyl Tylonolide" *The Journal of Antibiotics*, Oct. 1981, pp. 1374–1376.
"The Structure of Tylosin[1,2]", *Tetrahedron Letters*, No. 54, 1970, Pergamon Press, Great Britain, pp. 4737–4741.

Primary Examiner—Johnnie R. Brown
Assistant Examiner—Elli Peselev
Attorney, Agent, or Firm—Young & Thompson

[57] ABSTRACT

A compound of the formula

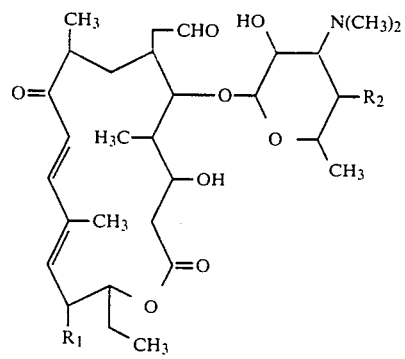

wherein $R_1$ is hydrogen, —COOR$_{11}$ or

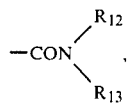

$R_{11}$ is optionally substituted lower alkyl, $R_{12}$ is optionally substituted hydrocarbon, heterocyclic or heterocyclic-lower alkyl, $R_{13}$ is hydrogen or lower alkyl, or $R_{12}$ and $R_{13}$ together constitute a heterocyclic ring together with the attached nitrogen atom, and $R_2$ is hydrogen or hydroxyl, or a pharmaceutically-acceptable salt thereof, has stronger antibacterial activity against Gram-positive bacteria than does tylosin. It is produced by deformylation, or by oxidizing a formyl at position-14, or by amidating the latter compound.

9 Claims, No Drawings

14-DE(HYDROXYMETHYL)-MYCAMINOSYL-TYLONOLIDE DERIVATIVES

This invention relates to novel 14-de(hydroxymethyl)-mycaminosyltylonolide derivatives. More particularly the present invention pertains to compounds of the formula

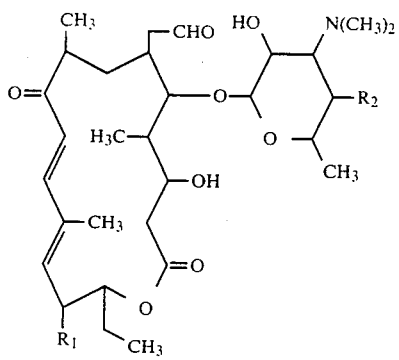

wherein $R_1$ is hydrogen, $-COOR_{11}$ or

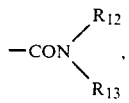

$R_{11}$ is optionally substituted lower alkyl, $R_{12}$ is optionally substituted hydrocarbon, heterocyclic or heterocyclic-lower alkyl, $R_{13}$ is hydrogen or lower alkyl, or $R_{12}$ and $R_{13}$ together constitute a heterocyclic ring together with the attached nitrogen atom, and $R_2$ is hydrogen or hydroxyl, or a pharmaceutically acceptable salt thereof.

The salts of compound [1] are pharmaceutically acceptable salts. Examples of the salt are salts of inorganic acids such as hydrochloric, sulfuric or phosphoric, or salts of organic acids such as acetates, propionates, tartrates, citrates, oxalates, succinates, malates, aspartates or glutamates. Other non-toxic salts may be formed.

The above novel compounds [1] have not only stronger antibacterial activity against Gram-positive bacteria as compared with known tylosin, but also they have extended antibacterial activity against resistant strains thereof and Gram-negative bacteria and are stable in vivo, and hence the said compounds [1] are useful as antibacterial agents having unexpectedly superior effects in clinical treatment when administered as oral or injectable preparations.

Furthermore the present compounds are useful in veterinary medicine or as feed additives for growth promotion.

The compounds of the present invention are named on the basis of a compound of the formula

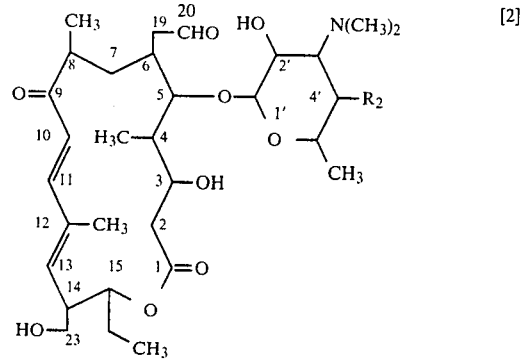

in which when $R_2$ is hydroxyl, the compound is O-mycaminosyltylonolide [Tetrahedron Letters, 4737-4740 (1970)] and when $R_2$ is hydrogen, the compound is 4'-deoxy-O-mycaminosyltylonolide [J. Antibiotics, 34(10), 1374-1376 (1981)].

Compound [1] of the present invention can be produced by the following processes:

[A] A compound [1], in which $R_1$ is hydrogen, of the formula [1a]:

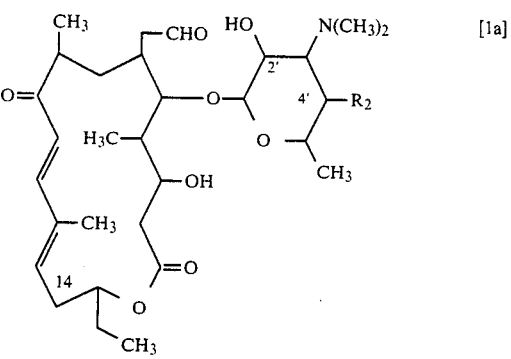

wherein $R_2$ is hydrogen or hydroxyl.

The compound hereinabove is produced by deformylation of a compound of the formula

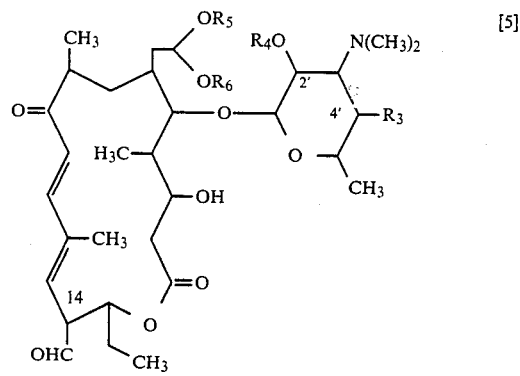

wherein $R_3$ is hydrogen or $-OR_4$, $R_4$ is a protective group for hydroxyl, $R_5$ and $R_6$ are lower alkyl or together form lower alkylene, followed by removal of the protective group for hydroxyl and the de-acetylation thereof.

A starting compound [5] of the present invention can be prepared by oxidizing a group $-CH_2OH$ to $-CHO$ in a compound of the formula

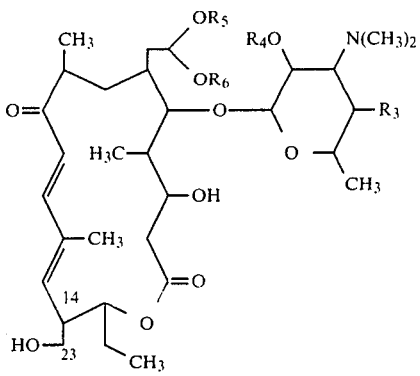

wherein $R_3$, $R_4$, $R_5$ and $R_6$ have the same meanings hereinabove, which is a compound wherein a hydroxyl group at position-2' and -4', or hydroxyl group at position-2' of formula [2] is protected and an aldehyde group thereof is protected by acetylation.

In the said process, the aldehyde therein may be previously protected by acetylation, thereafter the said hydroxy group may be protected.

Examples of the protective group for hydroxyl are lower alkanoyls such as acetyl, propionyl or butyryl and halogenated acetyls such as chloroacetyl, dichloroacetyl, trichloroacetyl or trifluoroacetyl. The acetyl group is preferred. Introduction of the acetyl group can be performed by reacting the compound [2] hereinbefore with acetic anhydride in an inert organic solvent such as dichloromethane, chloroform or acetone. The reaction proceeds at room temperature. The progress of the reaction can be traced by thin layer chromatography (TLC) or high performance liquid chromatography (HPLC) and the reaction can be stopped upon the disappearance of the compound [2] hereinbefore.

A compound of the formula

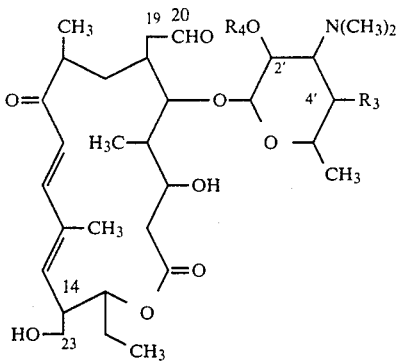

wherein $R_3$ and $R_4$ have the same meanings hereinbefore, can be isolated from the reaction mixture by adding water thereto and extracting with a water-immiscible organic solvent such as chloroform, dichloroethane, methylisobutyl ketone, ethyl acetate or butyl acetate at pH 8-9.5. Further purification can be performed by column chromatography using an adsorbent such as silica gel, active alumina or an adsorption resin, eluting with benzene-acetone or chloroform-methanol. A method for the production of compound [3] hereinbefore is given in Jap. Pat. Unexam. Publ. Nos. 57-5000 and 58-140096, and Jap. Pat. Appln. Nos. 57-78895 and 57-78897.

Acetylation hereinabove can be performed by any known acetylation method on compound [3], for example by reacting with a lower alcohol such as methanol or ethanol or a lower glycol such as ethylene glycol or propylene glycol in the presence of trifluoroacetic acid, trichloroacetic acid or p-toluenesulfonic acid. The thus-obtained acetal [4] can be isolated by the same procedure as for compound [3] hereinbefore. An example of the acetal [4] is illustrated in Jap. Pat. Unexam. Publ. No. 57-28100 and Jap. Pat. Appln. No. 57-78897.

Oxidation of —$CH_2OH$ at position-14 in acetal [4] to —CHO can be effected by reacting acetal [4] with a reaction product of $(CH_3)_2S$ and N-chlorosuccinimide in an inert organic solvent such as dichloroethane, benzene or toluene; by reacting acetal [4] with a reaction product of $(CH_3)_2SO$ and p-toluenesulfonyl chloride, p-toluenesulfonic anhydride or methanesulfonic anhydride; or by reacting acetal [4] and $(CH_3)_2SO$ with N,N'-dicyclohexylcarbodiimide in the presence of trifluoroacetic acid and treating the obtained sulfoxonium salt with base such as triethylamine or ammonia.

The thus-obtained starting material [5] can be isolated and purified by the same procedure as for compound [3] hereinbefore.

Deformylation of the starting compound [5] is effected by reacting the compound [5] with a tris-(trisphenylphosphine)rhodium halide such as $[(C_6H_5)_3P]_3RhCl$ in an inert organic solvent under heating.

The preferred organic solvents are benzene-series solvents such as benzene. Heating may be conducted with reflux of the reaction solvent. The progress of the reaction can be traced by TLC or HPLC and can be stopped upon the disappearance of the starting compound [5]. Isolation and purification of the reaction product of the formula [6].

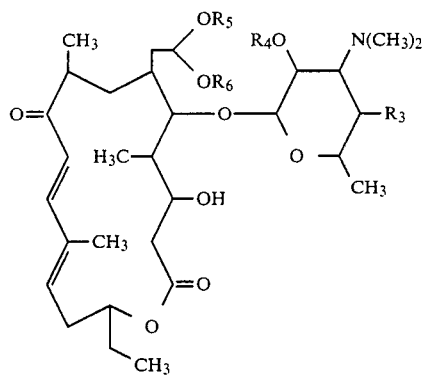

wherein $R_3$, $R_4$, $R_5$ and $R_6$ have the same meanings hereinbefore, can be performed by the same procedure as for compound [3] hereinbefore.

A protective group for hydroxyl, especially an acetyl group, in compound [6] can be removed by heating in an aqueous lower alcohol. Examples of lower alcohols are methanol and ethanol, preferably methanol. The progress of the reaction can be traced by TLC or HPLC and the reaction can be stopped upon the disappearance of compound [6]. Deacetylation of compound [6] can be performed by hydrolysis with acidic water. The said deacetylation may be performed prior to removal of the protective group by hydroxyl.

The product [1a] can be isolated by adjusting the reaction mixture to pH 9–10 with an aqueous alkali such as aqueous ammonia, extracting with a water-immiscible organic solvent such as chloroform, and distilling off the solvent therefrom. Further purification can be effected by any known isolation and purification procedure for known macrolide antibiotics, for example chromatography using silica gel, active alumina or an adsorption resin.

[B] A compound [1], in which R is —COOR$_{11}$, of the formula [1b]

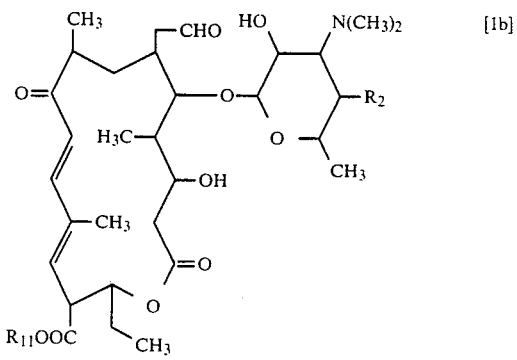

wherein R$_{11}$ is optionally substituted lower alkyl and R$_2$ is hydrogen or hydroxyl, can be prepared by esterifying a compound [7] of the formula

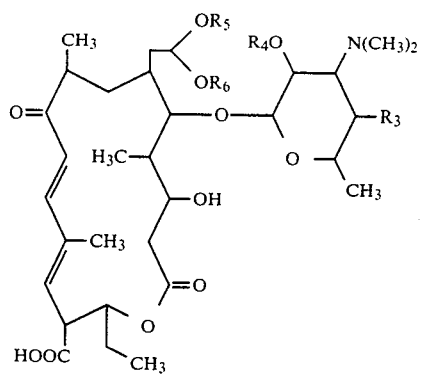

wherein R$_3$ is hydrogen or —OR$_4$, R$_4$ is a protective group for hydroxyl, R$_5$ and R$_6$ are lower alkyl or are together lower alkylene, with an alcohol of the formula

R$_{11}$—OH  [8]

wherein R$_{11}$ has the same meaning hereinbefore, removing the protective group for hydroxyl, and deacetylating.

Starting compound [7] can be obtained by oxidizing —CHO in compound [5] hereinbefore to —COOH. A method for the preparation of the above compound [5] is given in process [A] hereinabove.

The above oxidation of the intermediate compound [5] to obtain the starting compound [7] is effected by oxidation with a chlorate such as NaOCl$_2$ in an inert organic solvent such as acetone. The progress of the above reaction can be checked by TLC or HPLC and is terminated upon the disappearance of the intermediate [5].

The starting compound [7] can be obtained from the reaction mixture hereinabove by adjusting to pH 5–7 with an alkali such as aqueous ammonia, extracting with a water-immiscible organic solvent such as chloroform, and removing the solvent therefrom.

Esterification of the carboxyl in the starting compound [7] can be effected by any known esterification method. A preferred esterification method is the mixed anhydride method. For example, the starting compound [6] is reacted with a chloroformic acid ester such as ethyl chloroformate in the presence of a tertiary organic amine in an inert organic solvent, then reacted with the alcohol [8] hereinbefore.

Examples of the alcohol [8] are lower alcohols such as methanol, ethanol, propanol, isopropanol, butanol and isobutanol. They may be optionally substituted, preferably with lower alkoxy, lower alkoxycarbonyl or lower alkoxylower alkoxy.

The esterification reaction proceeds at room temperature and its progress can be traced by TLC or HPLC; then the reaction can be stopped upon achieving the maximum production of the reaction product of the formula

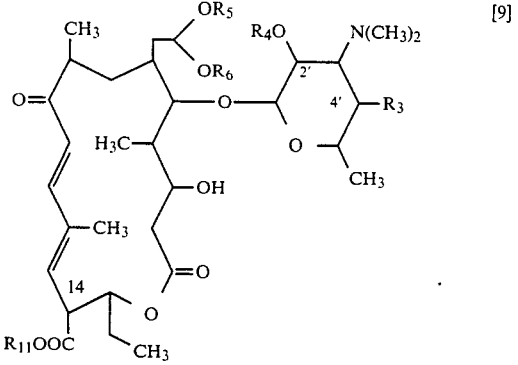

wherein R$_{11}$, R$_3$, R$_4$, R$_5$ and R$_6$ have the same meanings hereinbefore. Isolation and purification of the compound [8] from the reaction mixture can be performed by the same procedure as for the above compound [3].

The next step, the removal of the protective group for hydroxyl, especially the acetyl group in compound [9], can be performed by heating in an aqueous lower ethanol, methanol being preferred. The progress of the reaction can be tracted by TLC or HPLC and the reaction can be stopped upon the disappearance of compound [9].

Deacetylation of compound [9] is performed by hydrolyzing with acidic water. The said deacetylation may be performed prior to the removal of the protective group for hydroxyl.

The product [1b] can be obtained by the same procedure as the isolation and purification procedure of compound [1a] in process [A] hereinbefore. [C] A compound [1], in which R is

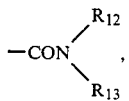

of the formula [1c]:

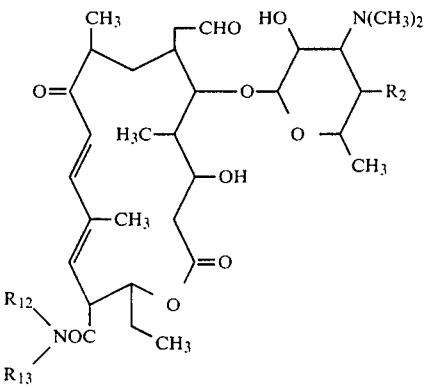

[1C]

wherein $R_2$ is hydrogen or hydroxyl, $R_{12}$ is an optionally substituted hydrocarbon, heterocyclic or heterocyclic-lower alkyl, $R_{13}$ is hydrogen or lower alkyl, or $R_{12}$ and $R_{13}$ together form a heterocyclic ring with the adjacent nitrogen atom.

A compound [1c] hereinabove can be obtained by treating compound [7] with an amine of the formula

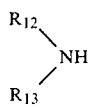

[10]

wherein $R_{12}$ and $R_{13}$ have the same meanings hereinbefore, to form an amide, then removing a protective group for hydroxyl and deacetylating the same.

Starting compound [7] can be prepared by the same procedure as the process [B] hereinbefore.

A known amidation process can be used for amidation of the carboxyl group in the starting compound [7]. The preferred amidation process is the mixed acid anhydride method. For example, the starting compound [7] is reacted with a chloroformic acid ester such as ethyl chloroformate in an inert organic solvent in the presence of a tertiary organic amine, and the amine [10] hereinbefore is reacted therewith.

Examples of the amine [10] are known primary amines, for example alkylamine, alkenylamine, cycloalkylamine, arylamine or aralkylamine. The hydrocarbon residue therein may optionally be substituted by one or more of lower alkoxy and lower alkoxy carbonyl. Furthermore, heterocyclic amines and heterocyclic-lower alkylamines can also be used. Secondary amines such as primary amines having an N-lower alkyl group can also be mentioned. Furthermore, 3-8 membered cyclic amines which may include nitrogen, oxygen or sulfur in the ring can be used.

The above amidation reaction proceeds at room temperature and its progress can be traced by TLC or HPLC, then the reaction may be stopped upon achieving the maximum production of a compound of the formula

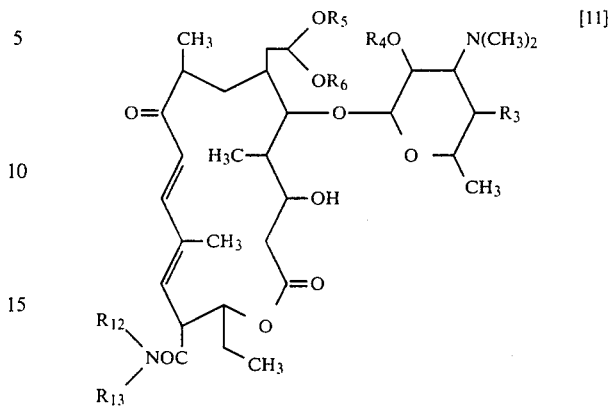

[11]

wherein $R_{12}$, $R_{13}$, $R_3$, $R_4$, $R_5$ and $R_6$ have the same meanings hereinbefore. The product [11] can be isolated and purified by the same procedure for compound [3] hereinbefore.

The next step is to remove the protective group for hydroxyl in compound [11], especially acetyl, and is performed by heating in an aqueous lower alcohol such as methanol or ethanol, of which methanol is preferred. The progress of the reaction can be traced by TLC or HPLC and the reaction can be stopped upon the disappearance of compound [11].

The deacetylation reaction can be effected by hydrolysis in acidic water. The said deacetylation may be performed prior to the removal of the protective group for hydroxyl.

Isolation of the compound [1c] can be effected by the same procedure as for compound [1a] hereinbefore.

The minimum inhibitory concentration (MIC) of compound [1] of the present invention is shown in Table 1. In Table 1, the abbreviations have the following meanings:
A: the product of Example 1.
B: the product of Example 2.
C: the product of Example 3.
D: the product of Example 4.
E: the product of Example 5.
F: the product of Example 6.
G: the product of Example 10.
H: the product of Example 11.
I: the product of Example 12.
TS: tylosin.
EM: erythromycin.

The test organisms were macrolide-antibiotics resistant A-group stains (clinical isolates of strains resistant to erythromycin, olenadomycin and 16-membered macrolide antibiotics).

TABLE 1

| | MIC (μg/ml) | | | | | | | | | | | |
|---|---|---|---|---|---|---|---|---|---|---|---|---|
| | Sample | | | | | | | | | | | |
| Test organisms | A | B | TS | C | D | E | F | G | H | I | EM | TS |
| Staph. aureus ATCC6538P | 0.2 | 0.2 | 0.8 | ≦0.05 | 0.2 | 0.1 | 0.1 | 0.4 | 0.2 | 0.1 | 0.2 | 0.8 |
| Staph. aureus MS353 | 0.2 | 0.2 | 0.8 | ≦0.05 | 0.2 | 0.1 | 0.1 | 0.4 | 0.2 | 0.1 | 0.2 | 0.8 |
| Staph. aureus MS353C36* | | | | ≦0.05 | 0.2 | 0.1 | 0.2 | 0.8 | 0.4 | 0.1 | >100 | >100 |
| Staph epidermidis ap-al-l | 0.1 | 0.1 | 0.4 | ≦0.05 | ≦0.05 | ≦0.05 | ≦0.05 | 0.2 | 0.1 | ≦0.05 | 0.1 | 0.4 |
| Strept. pyogenes N.Y.5 | ≦0.05 | ≦0.05 | 0.1 | ≦0.05 | ≦0.05 | ≦0.05 | ≦0.05 | ≦0.05 | ≦0.05 | ≦0.05 | ≦0.05 | 0.1 |
| Strept. pyogenes 1022* | >100 | 25 | >100 | >100 | >100 | >100 | >100 | >100 | >100 | >100 | >100 | >100 |
| Strept. faecalis 1501 | 0.2 | 0.4 | 1.6 | 0.1 | 0.2 | ≦0.05 | 0.2 | 0.2 | ≦0.05 | 0.2 | 0.2 | 1.6 |
| Strept. agalactiae 1020 | ≦0.05 | 0.1 | 0.4 | ≦0.05 | ≦0.05 | ≦0.05 | ≦0.05 | ≦0.05 | ≦0.05 | ≦0.05 | ≦0.05 | 0.4 |

TABLE 1-continued

| Test organisms | MIC (μg/ml) Sample | | | | | | | | | | |
|---|---|---|---|---|---|---|---|---|---|---|---|
| | A | B | TS | C | D | E | F | G | H | I | EM | TS |
| E. coli NIHJ-JC2 | 25 | 6.3 | >100 | | | | | | | | |
| Kleb. pneumoniae ATCC10031 | 1.6 | 0.8 | 50 | | | | | | | | |
| Proteus vulgaris OX19 | 6.3 | 3.1 | >100 | | | | | | | | |
| Serratia marcescens | 12.5 | 3.1 | >100 | | | | | | | | |

TABLE 1 (2)

| Test organisms | Sample | | | | | | | | |
|---|---|---|---|---|---|---|---|---|---|
| | C | D | E | F | G | H | I | EM | TS |
| Staph. aureus ATCC6538P | ≦0.05 | 0.2 | 0.1 | 0.1 | 0.4 | 0.2 | 0.1 | 0.2 | 0.8 |
| Staph. aureus MS353 | ≦0.05 | 0.2 | 0.1 | 0.1 | 0.4 | 0.2 | 0.1 | 0.2 | 0.8 |
| Staph. aureus MS353C36* | ≦0.05 | 0.2 | 0.1 | 0.2 | 0.8 | 0.4 | 0.1 | >100 | >100 |
| Staph epidermidis sp-al-1 | ≦0.05 | ≦0.05 | ≦0.05 | ≦0.05 | 0.2 | 0.1 | ≦0.05 | 0.1 | 0.4 |
| Strept. pyogenes N.Y.5 | ≦0.05 | ≦0.05 | ≦0.05 | ≦0.05 | ≦0.05 | ≦0.05 | ≦0.05 | ≦0.05 | 0.1 |
| Strept. pyogenes 1022* | >100 | >100 | >100 | >100 | >100 | >100 | >100 | >100 | >100 |
| Strept. faecalis 1501 | 0.1 | 0.2 | ≦0.05 | 0.2 | 0.2 | ≦0.05 | 0.2 | 0.2 | 1.6 |
| Strept. agalactiae 1020 | ≦0.05 | ≦0.05 | ≦0.05 | ≦0.05 | ≦0.05 | ≦0.05 | ≦0.05 | ≦0.05 | 0.4 |

The following examples illustrate the present invention. In the examples, the Rf-values indicated are taken by the following carrier and developers:

Carrier: Merck DC Fertigplatten Kieselgel 60 F$_{254}$, Art 5715.

Developer:
a: benzene-acetone (3:1)
b: benzene-acetone (5:1)
c: chloroform-methanol-conc. aq. ammonia (100:10:1)
d: chloroform-methanol (3:1)

EXAMPLE 1

2',4'-di-O-acetyl-O-mycaminosyltylonolide dimethylacetal

Trifluoroacetic acid (3 ml) was added to 2',4'-di-O-acetyl-O-mycaminosyltylonolide (4.23 g) dissolved in methanol (27 ml) and the mixture was stirred at room temperature for 2 hours. The reaction mixture was poured into 7% aqueous ammonia and extracted with chloroform. The chloroform layer was washed with water, filtered through Whatman 1PS filter paper, then dried in vacuo to obtain foamy solid 2',4'-di-O-acetyl-O-mycaminosyltylonolide dimethylacetal (3.96 g).

TLC: Rfa=0.35, Rfb=0.15

EXAMPLE 2

3',4'-di-O-acetyl-23-dedihydro-O-mycaminosyltylonolide dimethylacetal

Dimethylsulfide (1.03 ml) was quickly added under ice-cooling to N-chlorosuccinimide (1.37 g) dissolved in dry dichloromethane (40 ml) to form a white precipitate. The reaction mixture was cooled to −25° C. 2',4'-di-O-acetyl-O-mycaminosyltylonolide dimethylacetal (5.0 g) in dry dichloromethane (10 ml) was added thereto under argon over a period of 10 minutes and the mixture was stirred at −25° C. for 2 hours in an anhydrous condition. A methylene chloride solution (2 ml) of triethylamine (0.24 ml) was added thereto and the mixture was stirred for 5 minutes. The reaction mixture was warmed to room temperature, and water was added thereto, and it was then subjected to separation. The dichloromethane layer was filtered with Whatman 1PS filter paper and concentrated in vacuo. The residue was charge on a column of silica gel (Merck, Art 7734, 100 g) and eluted with benzene-acetone (12:1). The fractions showing Rfa=0.53 were collected and concentrated in vacuo to obtain the product (2.6 g).

PMR (CDCl$_3$, 100 MHz) $\delta_{ppm}^{TMS}$: 1.86 (s., 3H, 12—CH$_3$), 2.06 (s., 6H, OCOCH$_3$X2), 2.35 (s., 6H, —N(CH$_3$)$_2$), 3.22 (s., 3H, OCH$_3$), 3.29 (s., 3H, OCH$_3$), 4.39 (d., 1H, H-1'), 4.50 (d.d., 1H, H-20), 4.77 (t., 1H, H-4'), 4.91 (d.d., 1H, H-2'), 5.25 (d.t., 1H, H-15), 5.82 (d., 1H, H-13), 6.37 (d., 1H, H-10), 7.29 (d., 1H, H-11), 9.69 (d., 1H, CHO, J=2.7).

Mass (CI, isobutane): 726 (MH$^+$, very few), 694 (MH$^-$-32), 676, 664, 662, (694-32), 258, 216, 156, 129.

EXAMPLE 3

14-de(hydroxymethyl)-O-mycaminosyltylonolide

[(C$_6$H$_5$)$_3$P]$_3$RhCl (400 mg) was added to 2',4'-di-O-acetyl-23-dedihydro-O-mycaminosyltylonolide dimethylacetal (320 mg) dissolved in dry benzene (7.5 ml) and the mixture was refluxed at 80° C. for 1 hour. After detecting the disappearance of the starting material by silica gel TLC using benzene-acetone (3:1), the reaction mixture was concentrated in vacuo. The residue was charged on a column of silica gel (10 g, Merck, Art 9385) and eluted with benzene-acetone (20:1-15:1). The fractions eluting with benzene-acetone (18:1) were collected and concentrated in vacuo. Methanol (5 ml) was added to the residue and the material was refluxed for 16 hours. The reaction mixture was concentrated in vacuo, and the residue dissolved in benzene (10 ml) was extracted twice with 0.2N hydrochloric acid (25 ml). The aqueous layer was washed with hexane, stirred at room temperature for 1 hour and subjected to deacetylation. The reaction mixture was adjusted to pH 9 with dil. aq. ammonia, and extracted twice with chloroform (25 ml). The chloroform layer was filtered through Whatman 1PS filter paper and concentrated in vacuo. The residue was charged on a silica gel column (5 g, Merck, Art 9385) and eluted with chloroform-methanol (30:1) to obtain the product (90 mg).

PMR (CDCl$_3$, 100 MHz) $\delta_{ppm}^{TMS}$: 1.79 (s., 3H), 2.50 (s., 6H), 4.25 (d., 1H, H-1'), 5.08 (m., 1H, H-15), 5.91 (d.d., 1H, H-13, J=5.7 and 10 Hz), 6.23 (d., 1H, H-10), 7.33 (d., 1H, H-11), 9.70 (s., 1H, CHO).

Mass (CI, isobutane): 568 (MH$^+$), 174, 132.

EXAMPLE 4

2'-O-acetyl-4'-deoxy-O-mycaminosyltylonolide

Acetic anhydride (1.36 ml, 2.5 molar excess) was added to 4'-deoxy-O-mycaminosyltylonolide (3.35 g) dissolved in dichloromethane (20 ml) under ice cooling and the mixture was stirred at room temperature for 2.5 hours. The reaction mixture was poured into dil. aq. ammonia and extracted with chloroform at pH 8–9. The chloroform layer was filtered with Whatman 1PS filter paper and concentrated in vacuo to obtain 2'-O-acetyl-4'-deoxy-O-mycaminosyltylonolide. Yield: 3.56 g (yield: 99.1%).

TLC: Rfc=0.35

NMR (FX-100, CDCl$_3$) $\delta_{ppm}^{TMS}$: 1.82 (s., 3H, C$_{12}$—CH$_3$), 2.08 (s., 3H, OCOCH$_3$), 2.25 (s., 6H, —N(CH$_3$)$_2$), 3.74 (d., 2H, H-23), 4.24 (d., 1H, H-1'), 4.75 (d.d., 1H, H-2'), 4.96 (d.t., 1H, H-15), 5.88 (d., 1H, H-13), 6.32 (d., 1H, H-10), 7.34 (d., 1H, H-11), 9.69 (s., 1H, CHO)

Mass (CI): 624 (MH+), 606, 582, 218, 200.

EXAMPLE 5

2'-O-acetyl-4'-deoxy-O-mycaminosyltylonolide dimethylacetal

Trifluoroacetic acid (2.5 ml) was added to 2'-O-acetyl-4'-deoxy-O-mycaminosyltylonolide (5 g) dissolved in methanol (100 ml) and the mixture was stirred at room temperature for 4.5 hours. The end point of the reaction was detected by silica gel TLC when a spot of the starting material disappeared and a newly-appearing spot at Rfc=0.43 was confirmed. The reaction mixture was poured into dil. aq. ammonia (250 ml) and extracted twice with chloroform (250 ml). The chloroform layer was dehydrated with anhydrous magnesium sulfate and dried in vacuo to obtain foamy 2'-O-acetyl-4'-deoxy-O-mycaminosyltylonolide dimethylacetal (4.7 g).

EXAMPLE 6

14-de(hydroxymethyl)-4'-deoxy-O-mycaminosyltylonolide

Dimethylsulfide (0.816 ml) was added to N-chlorosuccinimide (600 mg) dissolved in dry dichloromethane (18 ml) under ice cooling. A dry dichloromethane (4 ml) solution of 2'-O-acetyl-4'-deoxy-O-mycaminosyltylonolide dimethylacetal (1.0 g) was added dropwise thereto at −25° C. under argon, and the mixture was stirred under anhydrous conditions at −25° C. for 2 hours. Triethylamine (0.865 ml) was added thereto and the mixture was stirred for 5 minutes. The reaction mixture was warmed to room temperature, washed with water and subjected to separation. The dichloromethane layer was filtered through Whatman 1PS filter paper and concentrated in vacuo. The residue was charged on a column of silica gel (20 g, Merck, Art 7734) and eluted with benzeneacetone (3:1). The fractions showing Rfa=0.2 were collected and concentrated in vacuo to obtain 2'-O-acetyl-23-dehydro-4'-deoxy-O-mycaminosyltylonolide dimethylacetal (163 mg), which was immediately dissolved in dry benzene (4 ml). [(C$_6$H$_5$)$_3$P]$_3$RhCl (220 mg) was added thereto, and the mixture was heated at 80° C. for 1 hour, then concentrated in vacuo. The residue was charged on a column of silica gel (5 g, Merck, Art 9385) and eluted with benzene-acetone (4:1) and concentrated in vacuo. Methanol was added to the residue and the material was heated at 55° C. for 16 hours. The reaction mixture was concentrated in vacuo. Acetonitrile-water-trifluoroacetic acid (3:2:0.1 v/v, 5.1 ml) was added to the residue and the material was stirred at room temperature for 2 hours for deacetylation. The reaction mixture was poured into ice water, adjusted to pH 9 and extracted twice with chloroform (20 ml). The chloroform layer was dried with anhydrous magnesium sulfate and concentrated in vacuo. The residue was charged on a column of silica gel (4 g) and eluted with chloroform-methanol (30:1) to obtain the product (38 mg).

PMR (CDCl$_3$, 100 MHz) $\delta_{ppm}^{TMS}$: 1.78 (s., 3H), 2.27 (s., 6H). 4.20 (d., 1H, H-1'), 5.07 (m., 1H, H-15), 5.92 (d.d., 1H, H-13), 6.30 (d., 1H, H-10), 7.34 (d., 1H, H-11), 9.72 (s., 1H CHO)

MS (CI, isobutane): 552 (MH+), 158, 116.

EXAMPLE 7

2',4'-di-O-acetyl-14-carboxy-14-de(hydroxymethyl)-O-mycaminosyltylonolide dimethylacetal 0.3M aqueous sulfamic acid (17.9 ml) and 0.2M aqueous sodium hypochlorite (19.3 ml) were added to 2',4'-di-O-acetyl-23-dedihydro-O-mycaminosyltylonolide dimethylacetal (2.6 g) dissolved in acetone (36 ml) and the mixture was stirred at room temperature for 30 minutes. The reaction mixture was adjusted to pH 5–6 with dil. aq. ammonia and extracted twice with chloroform (100 ml). The extract was dried with anhydrous magnesium sulfate and dried in vacuo to obtain the product (2.5 g).

TLC: Rfa=0, Rfd=0.66

PMR (CDCl$_3$, 100 MHz) $\delta_{ppm}^{TMS}$: 1.81 (s., 3H), 2.06, 2.07 (each s., 3H, OCOCH$_3$), 2.38 (s., 6H, —N(CH$_3$)$_2$), 3.22 (s., 3H, OCH$_3$), 3.29 (s., 3H, OCH$_3$), 4.40 (d., 1H, H-1'), 4.51 (br., 1H, H-20), 4.79 (t., 1H, H-4'), 4.93 (d.d., 1H, H-2'), 5.2 (m., 1H, H-15), 5.95 (d., 1H, H-13), 6.31 (d., 1H, H-10), 7.27 (d., 1H, H-11).

Mass (CI, isobutane): 666 (MH+-CO$_2$-32), 634 (666-32), 258, 216, 156, 129.

EXAMPLE 8

14-butyloxylcarbonyl-14-de(hydroxymethyl)-O-mycaminosyltylonodlide

Triethylamine (95 μl) was added to 2',4'-di-O-acetyl-14-carboxy-14-de(hydroxymethyl-O-mycaminosyltylonolide dimethylacetal (200 mg) dissolved in dichloromethane (2 ml), and ethyl chloroformate (49 μl) was added thereto at 0° C., then the mixture was stirred at 0° C. for 30 minutes. Butanol (05. ml) was added to the reaction mixture, and dimethylaminopyridine (approx. 10 mg) was added thereto, then the material was stirred at room temperature for 2 hours. The reaction mixture was poured into water (20 ml) and extracted twice with chloroform (20 ml). The chloroform layer was washed with saturated sodium chloride solution, filtered through Whatman 1PS filter paper and concentrated in vacuo. The residue was charged on a column of silica gel (Merck, Art 9385, 5 g) and eluted with benzene-acetone (15:1–12:1), then concentrated in vacuo. The residue dissolved in methanol (5 ml) was stirred at 55° C. overnight for deacetylation. The methanol was distilled off in vacuo, and the residue was dissolved in acetonitrile-water-trifluoroacetic acid (3:2:0.1 v.v, 5 ml) then stirred at room temperature for 1 hour for deacetylation. The reaction mixture was poured into ice water, adjusted to pH 9 by adding dil. aq. ammonia and extracted twice with chloroform (20 ml). The chloroform layer was dried with anhydrous magnesium sulfate and concentrated in vacuo to obtain the product (60 mg).

PMR (CECl₃, 100 MHz) $\delta_{ppm}^{TMS}$: 0.94 (t., 3H, —O(CH₂)₃C$\underline{H}$₃), 1.84 (s., 3H, 12—CH₃), 2.51 (s., 6H, —N(CH₃)₂), 4.14 (t., 2H, —C$\underline{H}$₂OOC—), 4.25 (d., 1H, h-1'), 5.25 (m., 1H, H-15), 5.91 (d., 1H, H-13), 6.32 (d., 1H, H-10), 7.30 (d., 1H, H-11, 9.70 (s., 1H, CHO).

Mass (CI, isobutane): 668 (MH+), 650, 192, 190, 174, 173, 151, 150, 133, 132.

EXAMPLE 9

14-(2-methoxyethyl)oxycarbonyl-14-de(hydroxymethyl)-O-mycaminosyltylonolide

In Example 8, butanol was replaced by 2-methoxyethanol to obtain the above-mentioned product. Yield: 60.5 mg.

PMR (CDCl₃, 100 MHz) $\delta_{ppm}^{TMS}$ 1.84 (s., 3H, 12—CH₃), 2.51 (s., 6H, N(CH₃)₂), 3.38 (s., 3H, OCH₃), 3.59 (t., 2H, CH₃OC$\underline{H}$₂—CH₂O—), 4.25 (d., 1H, H-1'), 4.30 (t., 2H, —C$\underline{H}$₂OOC—), 5.25 (m., 1H, H-15), 5.93 (d., 1H, H-13), 6.33 (d., 1H, H-10), 7.31 (d., 1H, H-13), 9.70 (s., 1H, CHO).

Mass (CI, isobutane): 670 (MH+), 192, 174, 133.

EXAMPLE 10

14-isopropyloxycarbonyl-14-de(hydroxymethyl)-O-mycaminosyltylonolide:

In Example 8, butanol was replaced by isopropanol to obtain the product mentioned hereinabove. Yield: 59 mg.

PMR (CDCl₃, 100 MHz) $\delta_{ppm}^{TMS}$: 1.27 (d., 6H,

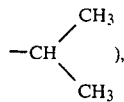

1.84 (s., 3H, 12—CH₃), 2.50 (s., 6H, —N(CH₃)₂), 4.25 (d., 1H, H-1'), 5.05 (m., 1H, —O—CH(CH₃)₂), 5.24 (m., 1H, H-15), 5.91 (d., 1H, H-13), 6.32 (d., 1H, H-10), 7.31 (d., 12H, H-11), 9.70 (s., 1H, CHO).

Mass (CI, isobutane): 654 (MH+), 636, 192, 174, 132.

EXAMPLE 11

14-ethyloxycarbonyl-14-de(hydroxymethyl)-O-mycaminosyltylonolide

In Example 8, butanol was replaced by ethanol to obtain the product. Yield: 83.4 mg.

PMR (CDCl₃, 100 MHz) $\delta_{ppm}^{TMS}$: 1.28 (t., 3H, —CH₂C$\underline{H}$₃), 1.84 (s., 3H, 12—CH₃), 2.50 (s., 6H, —N(C$\underline{H}$₃)₂), 4.20 q., 2H, —OC$\underline{H}$₂CH₃), 4.25 (d., 1H, H-1'), 5.25 (m., 1H, H-15), 5.92 (d., 1H, H-13), 6.32 (d., 1H, H-10), 7.30 (d., 1H, H-11), 9.70 (s., 1H, CHO).

Mass (CI, isobutane): 640 (MH+), 622, 192, 190, 174, 133, 132.

EXAMPLE 12

14-{1-[ethyloxycarbonyl)ethyl]oxydicarbonyl}-14-de(hydroxymethyl)-O-mycaminosyltylonolide In Example 8, butanol was replaced by ethyl lactate to obtain the product. Yield: 83.4 mg.

PMR (CDCl₃, 100 MHz) $\delta_{ppm}^{TMS}$: 1.27 (t., 3H), 1.51, 1.53 (d., 3H, —OCHC$\underline{H}$₃), 1.84 (s., 3H, 12—CH₃), 2.51 (s., 6H), 4.20 (q., 2H, —COOC$\underline{H}$₂CH₃), 4.25 (d., 1H, H-1'), 5.10 (m., 1H, —OC$\underline{H}$—), 5.25 (m., 1H, H-15), 5.91 (d., 1H, H-13), 6.32 (d., 1H, H-10), 7.31 (d., 1H, H-11), 9.70 (s., 1H, CHO).

Mass (CI, isobutane): 721(MH+), 640, 626, 504, 174, 133.

EXAMPLE 13

14-[(2-ethyloxycarbonyl)isopropyl]oxycarbonyl-14-de(hydroxymethyl)-O-mycaminosyltylonolide In Example 8, butanol was replaced by ethyl 2-hydroxy-lactate to obtain the product. Yield: 74.2 mg.

PMR (CECl₃, 100 MHz) $\delta_{ppm}^{TMS}$: 1.26 (t., 3H), 1.83 (s., 3H, 12—CH₃), 2.50 (s., 6H), 4.20 (m., 2H, —OCH₂CH₃), 4.25 (d., 2H, H-1'), —5.3 (d., 1H, H-13), 6.32 (d., 1H, H-10), 7.30 (d., 1H, H-11); 9.70 (s., 1H, CHO).

Mass (CI, isobutane): 726 (MH+), 640, 626, 192, 174, 165, 133, 115.

EXAMPLE 14

14-{2-[(2-methoxyethyloxy)ethyl]oxycarbonyl}-14-de(hydroxymethyl)-O-mycaminosyltylonolide In Example 8, butanol was replaced by 2-(2-methoxyethoxy)ethanol to produce the product. Yield: 54 mg.

PMR (CDCl₃, 100 MHz) $\delta_{ppm}^{TMS}$: 1.83 (s., 3H), 2.51 (s., 6H), 3.38 (s., 3H, OCH₃), 4.25 (d., 1H, H-1'), 4.29 (t., 2H, —CH₂CH₂OOC—), 5.25 (m., 1H, H-15), 5.90 (d., 1H, H-13), 6.32 (d., 1H, H-10), 7.30 (d., 1H, H-11), 9.70 (s., 1H, CHO).

Mass (CI, isobutane): 714 (MH+), 506, 253, 192, 177, 174, 133.

EXAMPLE 15

14-butylcarbamoyl-14-de(hydroxymethyl)-O-mycaminosyltylonolide

Triethylamine (95 μl) was added to 2',4'-di-O-acetyl-23-dedihydro-O-mycaminosyltylonolide (200 mg) dissolved in dry dichloromethane (2 ml). Ethyl chloroformate (49 μl) was added thereto under cooling at 0° C. for 30 min. Butylamine (0.27 ml) was added thereto and the material was stirred at room temperature for 1 hour. Chloroform (20 ml) was added thereto and the mixture was washed with dil. hydrochloric acid, water and dil. aq. ammonia. The chloroform layer was filtered through Whatman 1PS filter paper and concentrated in vacuo. The residue was charged on a column of silica gel (5 g, Merck, Art 9385), eluted with benzene-acetone (6:1–4:1) and concentrated in vacuo. The residue was dissolved in methanol (5 ml) and heated at 55° C. overnight for deacetylation. The methanol was removed in vacuo and the residue dissolved in acetonitrile-water-trifluoroacetic acid (3:2:0.1 v/v, 5 ml) was stirred at room temperature for 1 hour for deacetylation. The reaction mixture was poured into water (10 ml), adjusted to pH 9 with dil. aq. ammonia and extracted twice with chloroform (20 ml). The chloroform layer was dried with anhydrous magnesium sulfate and dried in vacuo to obtain the product (76 mg).

Mass (CI, isobutane): 667 (MH+), 649, 192, 174, 133.

PM (CDCl₃, 100 MHz) $\delta_{ppm}^{TMS}$: 0.98 (t., 3H, —NH(CH₂)₃C$\underline{H}$₃), 1.83 (s., 3H, 12—CH₃), 2.50 (s., 6H, —N(CH₃)₂), 4.25 (d., 1H, H-1'), 5.29 (d.t., 1H, H-15), 5.71 (t., 1H, NH), 5.95 (d., 1H, H-13), 6.32 (d., 1H, H-10), 7.30 (d., 1H, H-11), 9.69 (s., 1H, CHO).

EXAMPLE 16

14-benzylcarbamoyl-14-de(hydroxymethyl)-O-mycaminosyltylonolide

In Example 15, butylamine (0.27 ml) was replaced by benzylamine (0.3 ml) to obtain the product. Yield: 85.6 mg.

Mass (CI, isobutane): 701 (MH+), 683, 493, 475, 192, 174, 133.

PMR (CDCl$_3$, 100 MHz) $\delta_{ppm}^{TMS}$: 1.80 (s., 3H, 12—CH$_3$). 2.51 (s., 6H, —N(CH$_3$)$_2$), 4.24 (d., 1H. H-1'), 4.44 (d., 2H, —CH$_2$NH—), 5.29 (d.t., 1H, H-15), 5.95 (d., 1H, H-13), 6.00 (br.t., 1H, NH), 6.30 (d., 1H, H-10), 7.1–7.4 (6H, H-11, phenyl proton), 9.68 (s., 1H, CHO).

EXAMPLE 17

14-(N-methyl-benzylcarbamoyl)-14-de(hydroxymethyl)-O-mycaminosyltylonolide

In Example 15, butylamine (0.27 ml) was replaced by N-methyl-benzylamine (0.35 ml) to obtain the product. Yield: 60.5 mg.

Mass (CI, isobutane): 715 (MH+), 697, 507, 192, 190, 174.

PMR (CDCl$_3$, 100 MHz) $\delta_{ppm}^{TMS}$: 1.69, 1.87 (each br. s., 3H, 12—CH$_3$), 2.50 (s., 6H, —N(CH$_3$)$_2$), 2.85, 3.01 (each s., 3H, —CONCH$_3$), 4.25 (br., d., 1H, H-1'), 4.47, 4.59 (each br.s., 2H, —CH$_2$NCH$_3$), 5.5 (m., 1H, H-15), 5.92 (br., d., 1H, H-13), 6.29, 6.35 (each br.d., 1H, H-10), 7.0–7.4 (6H, H-11, phenyl proton), 9.70 (s., 1H, CHO).

EXAMPLE 18

14-diethylcarbamoyl-14-de(hydroxymethyl)-O-mycaminosyltylonolide

In Example 15, butylamine (0.27 ml) was replaced by diethylamine (0.28 ml) to obtain the product. Yield: 53 mg.

Mass (CI, isobutane): 667 (MH+), 649, 476, 192, 190, 174, 156, 132.

IR (KBr): 1640 cm$^{-1}$ (—CON—)

PMR (CDCl$_3$, 100 MHz) $\delta_{ppm}^{TMS}$: 1.17 (t., 6H,

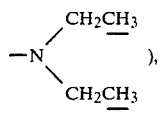

1.87 (s., 3H, 12—CH$_3$), 2.50 (s., 6H, —N(CH$_3$)$_2$), 4.25 (d., 1H, H-1'), 5.47 (d.t., 1H, H-15), 5.91 (d., 1H, H-13), 6.35 (d., 1H, H-10), 7.33 (d., 1H, H-11), 9.70 (s., 1H, CHO).

EXAMPLE 19

14-dimethylcarbamoyl-14-de(hydroxymethyl-O-mycaminosyltylonolide

In Example 15, butylamine (0.27 ml) was replaced by dimethylamine hydrochloride (223 mg) and triethylamine (0.38 ml) dissolved in dichloromethane (4 ml) to obtain the product. Yield: 49 mg.

Mass (CI, isobutane): 639 (MH+), 621, 192, 174, 132.

PMR (CDCl$_3$, 100 MHz) $\delta_{ppm}^{TMS}$: 1.89 (s., 3H, 12—CH$_3$), (s., 6H, —N(CH$_3$)$_2$), 2.97 (s., 6H,

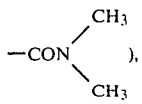

4.25 (d., 1H, H-1'), 5.46 (d.t., 1H, H-15), 5.94 (d., 1H, H-13), 6.35 (d., 1H, H-10), 7.32 (d., 1H, H-11), 9.70 (s., 1H, CHO).

What is claimed is:

1. A compound of the formula

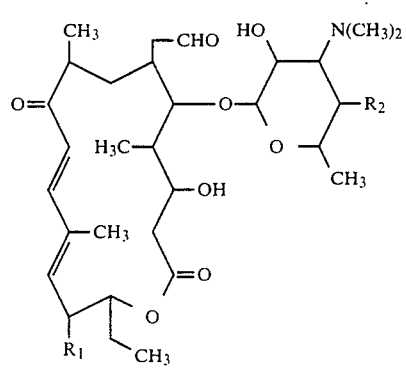

wherein R$_1$ is hydrogen, —COOR$_{11}$ or

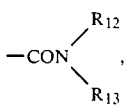

R$_{11}$ is hydrogen, lower alkyl, lower alkoxy-lower alkyl, lower alkoxycarbonyl-lower alkyl or lower alkoxy-lower alkoxy-lower alkyl, R$_{12}$ is lower alkyl or phenyl-lower alkyl, R$_{13}$ is hydrogen or lower alkyl, R$_2$ is hydrogen or hydroxyl, or a pharmaceutically-acceptable salt thereof.

2. A compound according to claim 1 wherein R$_1$ is hydrogen.

3. A compound according to claim 2 wherein said compound is a compound selected from the group consisting of 14-de(hydroxymethyl)-O-mycaminosyltylonolide and 14-de(hydroxymethyl)-4'-deoxy-O-mycaminosyltylonolide.

4. A compound according to claim 1 wherein R$_1$ is —COOR$_{11}$, and R$_{11}$ is hydrogen, lower alkyl, lower alkoxy-lower alkyl, lower alkoxycarbonyl-lower alkyl or lower alkoxy-lower alkoxy-lower alkyl.

5. A compound according to claim 4 wherein said compound is a compound selected from the group consisting of the following:

14-butyloxycarbonyl-14-de(hydroxymethyl)-O-mycaminosyltylonolide, 14-(2-methoxyethyl)oxycarbonyl-14-de(hydroxymethyl-O-mycaminosyltylonolide, 14-isopropyloxycarbonyl-14-de(hydroxymethyl)-O-mycaminosyltylonolide, 14-ethyloxycarbonyl-14-de(hydroxymethyl)-O-mycaminosyltylonolide, 14-{1-[(ethyloxycarbonyl)ethyl]oxycarbonyl}-14-de(hydroxymethyl)-O-mycaminosyltylonolide, 14-[(2-ethyloxycarbonyl)isopropyl]oxycarbonyl-14-de(hydroxymethyl)-O-mycaminosyltylonolide, and 14-{2-[(2-methoxyethyloxy)ethyl]oxycarbonyl}-14-de(hydroxymethyl)-O-mycaminosyltylonolide.

6. A compound according to claim 1 wherein $R_1$ is

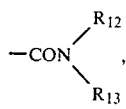

$R_{12}$ is lower alkyl or phenyl-lower alkyl and $R_{13}$ is hydrogen or lower alkyl.

7. A compound according to claim 6 wherein said compound is a compound selected from the group consisting of the following:

14-butylcarbamoyl-14-de(hydroxymethyl)-O-mycaminosyltylonolide, 14-benzylcarbamoyl-14-de(hydroxymethyl)-O-mycaminosyltylonolide, 14-(N-methyl-benzylcarbamoyl)-14-de(hydroxymethyl)-O-mycaminosyltylonolide, and 14-diethylcarbamoyl-14-de(hydroxymethyl)-O-mycaminosyltylonolide.

8. A compound of the formula

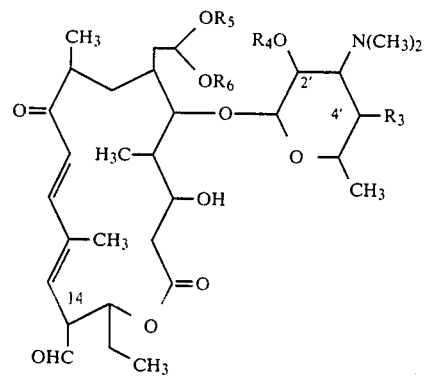

wherein $R_3$ is hydrogen or —$OR_4$, $R_4$ is lower alkanoyl or halogenated acetyl, $R_5$ and $R_6$ are lower alkyl or together form lower alkylene.

9. A compound of the formula

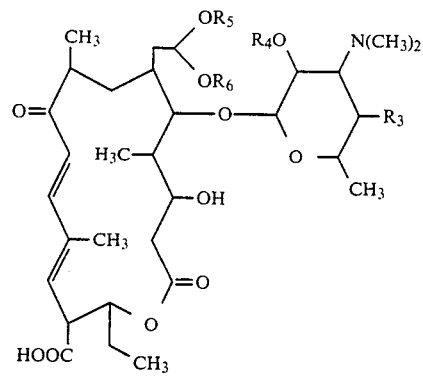

wherein $R_3$ is hydrogen or —$OR_4$, $R_4$ is lower alkanoyl or halogenated acetyl, $R_5$ and $R_6$ are lower alkyl or together form lower alkylene.

* * * * *